(12) United States Patent
Kato et al.

(10) Patent No.: US 7,232,904 B2
(45) Date of Patent: Jun. 19, 2007

(54) CRYSTAL OF ARYLETHENESULFONAMIDE DERIVATIVE AND PREPARATION PROCESS THEREOF

(75) Inventors: Yoshinori Kato, Takahagi (JP); Hironori Harada, Tsukuba (JP); Masahiro Kurotani, Takahagi (JP); Haruhiko Toda, Takahagi (JP); Kenichirou Sakamoto, Takahagi (JP)

(73) Assignee: Astellas Pharma Inc. (JP)

( * ) Notice: Subject to any disclaimer, the term of this patent is extended or adjusted under 35 U.S.C. 154(b) by 354 days.

(21) Appl. No.: 10/484,836

(22) PCT Filed: Jul. 25, 2002

(86) PCT No.: PCT/JP02/07551

§ 371 (c)(1),
(2), (4) Date: Jan. 26, 2004

(87) PCT Pub. No.: WO03/010152

PCT Pub. Date: Feb. 6, 2003

(65) Prior Publication Data

US 2004/0162302 A1    Aug. 19, 2004

(30) Foreign Application Priority Data

Jul. 27, 2001    (JP) .............................. 2001-227253

(51) Int. Cl.
*C07D 239/48*    (2006.01)
*C07D 239/54*    (2006.01)

(52) U.S. Cl. ...................................................... 544/296
(58) Field of Classification Search ................. 544/296
See application file for complete search history.

(56) References Cited

U.S. PATENT DOCUMENTS 6,083,955 A    7/2000    Harada et al.

FOREIGN PATENT DOCUMENTS

WO    WO 97/22595    6/1997

OTHER PUBLICATIONS

Ulrich, Chapter 4: Crystallization, Kirk-Othmer Encyclopedia of Chemical Technology, Aug. 2002.*
Vippagunta et al., Cyrstalline Solids, Advanced Drug Delivery Reviews, 48, pp. 3-26, 2001.*
West, Solid Solutions, Solid State Chemistry and its applications, pp. 358 & 365, 1988.*

* cited by examiner

*Primary Examiner*—Deepak Rao
(74) *Attorney, Agent, or Firm*—Finnegan, Henderson, Farabow, Garrett & Dunner LLP (57) ABSTRACT

Novel crystals of a potassium salt of (E)-N-[6-methoxy-5-(2-methoxyphenoxy)-2-(pyrimidin-2-yl)pyrimidin-4-yl]-2-phenylethenesulfonamide, a preparation process thereof, and novel solvates of (E)-N-[6-methoxy-5-(2-ethoxyphenoxy)-2-(pyrimidin-2-yl)pyrimidin-4-yl]-2-phenylethenesulfonamide.

15 Claims, 12 Drawing Sheets

CRYSTAL OF ARYLETHENESULFONAMIDE DERIVATIVE AND PREPARATION PROCESS THEREOF

This application is a national stage entry under 35 U.S.C. § 371 of PCT/JP02/07551, filed Jul. 25, 2002.

TECHNICAL FIELD

The present invention relates to novel crystals of a potassium salt of (E)-N-[6-methoxy-5-(2-methoxyphenoxy)-2-(pyrimidin-2-yl)pyrimidin-4-yl]-2-phenylethenesulfonamide (hereinafter referred to as "Compound A"), a Compound A ethyl acetate and a Compound A ethanolate, each of which is a novel solvate of Compound A, and a preparation process for an α-type crystal of a potassium salt of Compound A.

BACKGROUND ART

Endothelin (hereinafter referred to as "ET") is an endogenous physiologically active peptide consisting of 21 amino acids, and known to exist as 3 types of iso-peptides, i.e., ET-1, ET-2 and ET-3, of which the amino acid sequences are slightly different each other. ET binds to the ET receptor on the target cellular membrane to exhibit a physiological activity. Up to now, as for the ET receptor, it is known that there are at least 2 sub-types, i.e., $ET_A$ and $ET_B$. $ET_A$ receptor has higher affinity to ET-1 and ET-2 than to ET-3, and $ET_B$ receptor has the same degree of affinity to ET-1, ET-2 and ET-3.

It is reported that a potassium salt of Compound A has a chemical structure represented by the following formula (I), has a high affinity with ET receptors, particularly an $ET_A$ receptor, has an action to competitively inhibit binding to ET receptors, and is useful as a therapeutic drug for various diseases in which ET is involved, including cardiovascular diseases, such as essential hypertension (see WO 97/22595).

(I)

Example 15(a) of the foregoing document discloses a preparation process for a potassium salt of Compound A in a small amount at the laboratory level and describes that 320 mg of a potassium salt of Compound A is obtained by recrystallization from an ethanol-water mixed solvent and that the resulting crystal has a melting point of from 201 to 203° C.

Also, Example 2 of the foregoing document discloses Compound A and a preparation process in a small amount at the laboratory level as its preparation example and describes that 273 mg of Compound A is obtained by crystallization from diethyl ether as a solvent after column chromatography purification.

However, the foregoing document does not disclose or suggest at all that the potassium salt of Compound A exhibits crystal polymorphism and that a Compound A ethyl acetate and a Compound A ethanolate are stably present.

Also, for the purpose of mass-production of a potassium salt of Compound A, the present inventors made investigations about industrial manufacturing of a potassium salt of Compound A having the same quality. However, a potassium salt of Compound A having a melting point of from 201 to 203° C. as disclosed in the forgoing document could not be obtained.

Accordingly, it has been desired to establish a preparation process for a crystal of a potassium salt of Compound A having the same quality, which can be expected to have a constant operation/working-effect and is suitable as a pharmaceutical bulk drug, with good reproducibility and in high yield.

Also, though the foregoing document describes Compound A that is a process intermediate of the potassium salt of Compound A and a preparation process, since purification by a column chromatography is needed, such was not desirable on the industrial manufacturing. For this reason, it has been desired to establish a preparation process for obtaining Compound A, a salt thereof, a solvate thereof, or a solvate of a salt thereof without need of purification by a column chromatography which likely complicates the operation on the industrial manufacturing.

Disclosure of Invention

Under such technical levels, the present inventors made extensive and intensive investigations on how to provide crystals of a potassium salt of Compound A. As a result, it has surprisingly been found that a formed crystal changes depending upon the detailed preparation condition, that is, crystal polymorphism is present in the potassium salt of Compound A.

Usually, since in a compound in which crystal polymorphism is present, various properties differ depending on the crystal form, even the same compound may possibly exhibit a quite different operation/working-efficacy. In particular, in drugs, in the case where it is assumed that compounds having a different operation/working-effect have the same effect, it may be considered that an operation/working-effect that is different from one as assumed occurs, leading to an unforeseen situation. Therefore, it is demanded to provide a compound having the same quality, which can be always expected to have a constant operation/working-effect. Accordingly, in the case where a compound in which crystal polymorphism is present is used as a drug, for the sake of ensuring a uniform quality and a constant operation/working-effect required as a drug, it is necessary to provide a certain single crystal of that compound always fixedly.

In addition, as a result of further investigations on the crystal polymorphism of Compound A, novel three kinds of crystals each having a melting point different from that of the crystal of the potassium salt of Compound A disclosed in the foregoing document have been found. As a result of analysis of crystallographic data and physicochemical properties of these crystals, it has been found that any of these novel crystals have excellent properties as a pharmaceutical bulk drug, such as heat stability, solubility in aqueous solvents, biological utilization capability, and low electrifi cation. That is, it has been found that an α-type crystal of the potassium salt of Compound A has high water solubility as compared with other two kinds of crystals and hence, is advantageous from the viewpoint of formulation, and can be expected to have an operation/working-effect such as enhancement of absorption as an oral drug; a β-type crystal of the potassium salt of Compound A has a high melting point and is excellent in heat stability; and since a γ-type crystal of the potassium salt of Compound A has a higher melting point, is low in hygroscopicity and excellent in stability, and has low electrification and high fluidity, it is excellent in industrial manufacturing, especially in filtration performance.

Also, in manufacturing general compounds, when the degree of purification of a process intermediate thereof is high, it is possible to obtain a desired compound having a high purity, and hence, such is advantageous on the preparation. However, purification using a column chromatography is not desired because it complicates the operation on the industrial manufacturing.

Here, with respect to Compound A as the process intermediate of the potassium salt of Compound A, novel two kinds of solvates, i.e., a Compound A 0.4 ethyl acetate and a Compound A monoethanolate, which do not require purification by a column chromatography that is necessary for the preparation process of Compound A described in the prior art documents during the purification, have been found. As a result of measurement of the purity of these solvates, it has been found that the purification effect of the Compound A 0.4 ethyl acetate is higher than that of the Compound A monoethanolate. Accordingly, it has been found that the Compound A 0.4 ethyl acetate is the most suitable as a process intermediate in the industrial manufacturing of the potassium salt of Compound A among Compound A, salts thereof, solvates thereof and solvates of salts thereof and that in preparing the potassium salt of Compound A, it is most industrially advantageous to employ a preparation process via the Compound A 0.4 ethyl acetate.

On the other hand, in preparing the potassium salt of Compound A using the Compound A 0.4 ethyl acetate as a process intermediate, excessive consumption of potassium hydroxide by ethyl acetate, which is used in preparing the potassium salt of Compound A as a process intermediate of Compound A, a salt thereof, a solvate thereof, or a solvate of a salt thereof, and contamination of ethyl acetate into the potassium salt of Compound A as the ultimate bulk can be prevented by preparing the potassium salt of Compound A using the Compound A monoethanolate as a process intermediate.

Accordingly, the invention has been accomplished based on these findings. According to the invention, there are provided an α-type crystal of a potassium salt of Compound A; an α-type crystal of a potassium salt of Compound A, characterized by having main peaks in the vicinity of lattice spacings of 12.00, 9.52, 4.77, 4.23 and 4.08 angstroms in the powder X-ray diffraction spectrum obtained using a Cu—Kα line; preferably, an α-type crystal of a potassium salt of Compound A, characterized having the lattice spacings and relative intensities shown in Table 1 in the powder X-ray diffraction spectrum obtained using a Cu—Kα line; and an α-type crystal of a potassium salt of Compound A having a melting point of 196 to 198° C.

TABLE 1

| lattice spacing/Å | relative intensity | lattice spacing/Å | relative intensity |
|---|---|---|---|
| 13.42 | slightly strong | 4.23 | strong |
| 12.00 | strong | 4.08 | strong |
| 9.52 | strong | 3.87 | slightly strong |
| 7.46 | medium | 3.65 | slightly strong |
| 6.72 | medium | 3.46 | slightly strong |
| 5.43 | medium | 3.31 | medium |
| 4.77 | strong | 3.03 | medium |

Also, according to the invention, there are provided a β-type crystal of a potassium salt of Compound A; a β-type crystal of a potassium salt of Compound A, characterized by having main peaks in the vicinity of lattice spacings of 11.65 and 4.66 angstroms in the powder X-ray diffraction spectrum obtained using a Cu—Kα line; preferably, a β-type crystal of a potassium salt of Compound A, characterized having the lattice spacings and relative intensities shown in Table 2 in the powder X-ray diffraction spectrum obtained using a Cu—Kα line; and a β-type crystal of a potassium salt of Compound A having a melting point of 231 to 233° C.

TABLE 2

| lattice spacing/Å | relative intensity | lattice spacing/Å | relative intensity |
|---|---|---|---|
| 11.65 | strong | 4.09 | medium |
| 9.65 | medium | 3.99 | slightly strong |
| 8.60 | medium | 3.88 | slightly strong |
| 5.13 | slightly strong | 3.69 | slightly strong |
| 4.79 | medium | 3.41 | medium |
| 4.66 | strong | 3.17 | medium |
| 4.36 | medium | 3.08 | medium |
| 4.22 | slightly strong | | |

Also, according to the invention, there are provided a γ-type crystal of a potassium salt of Compound A; a γ-type crystal of a potassium salt of Compound A, characterized by having main peaks in the vicinity of lattice spacings of 11.10, 4.92, 4.67, 4.23, 4.18, 4.10, 3.47 and 3.44 angstroms in the powder X-ray diffraction spectrum obtained using a Cu—Kα line; preferably, a γ-type crystal of a potassium salt of Compound A, characterized by having the lattice spacings and relative intensities shown in Table 3 in the powder X-ray diffraction spectrum obtained using a Cu—Kα line; and a γ-type crystal of a potassium salt of Compound A having a melting point of from 251 to 254° C.

TABLE 3

| lattice spacing/Å | relative intensity | lattice spacing/Å | relative intensity |
|---|---|---|---|
| 11.10 | strong | 4.51 | slightly strong |
| 9.24 | medium | 4.23 | strong |
| 8.65 | slightly strong | 4.18 | strong |
| 4.92 | strong | 4.10 | strong |
| 4.87 | slightly strong | 3.47 | strong |
| 4.78 | slightly strong | 3.44 | strong |
| 4.67 | strong | | |

Incidentally, in the powder X-ray diffraction spectrum, the crystal lattice spacings and overall pattern are important in approval of identity of the crystal from the viewpoint of properties of data, and since the relative intensity can somewhat change depending upon the direction of crystal growth, the size of particles, and the measurement condition, it should not be strictly considered. Also, while the invention relates to a pure α-type crystal of a potassium salt of Compound A; a pure β-type crystal of a potassium salt of Compound A; and a pure γ-type crystal of a potassium salt of Compound A, the invention also includes mixtures that can be substantially regarded in the same light as these pure α-type, β-type and γ-type crystals.

In addition, according to the invention, there are provided a Compound A ethyl acetate and a Compound A ethanolate, and preferably a Compound A 0.4 ethyl acetate and a Compound A monoethanolate, each of which is useful as a process intermediate of an α-type crystal of a potassium salt of Compound A.

Also, according to the invention, there is provided a preparation process of an α-type crystal of a potassium salt of Compound A, characterized by exerting potassium hydroxide or potassium carbonate, and preferably potassium hydroxide, to Compound A, a salt thereof, a solvate thereof or a solvate of a salt thereof, and preferably a Compound A 0.4 ethyl acetate or a Compound A monoethanolate, in an ethanol-water mixed solvent, dissolving therein, and then crystallizing out of the solution in a water-ethanol mixed solvent having a ratio of water to ethanol of 1:12.5 or more.

[Preparation Process]

The invention will be hereunder described in detail.

The α-type crystal of the potassium salt of Compound A of the invention can be prepared by adding and dissolving Compound A, a salt thereof, a solvate thereof or a solvate of a salt thereof in a solution of a reaction-corresponding amount or an excessive amount of potassium hydroxide or potassium carbonate in an ethanol-water based mixed solvent (with stirring upon heating, if desired) and after filtering insoluble materials, allowing the residue to stand for cooling and crystallization at room temperature.

At this time, since the potassium salt of Compound A has properties such that it is sparingly soluble in ethanol, in dissolving the potassium salt of Compound A in the ethanol-water based mixed solvent, it is preferable to dissolve it in a mixed solvent having a volume ratio of water to ethanol of about 1:10.

Also, during the crystallization, it is possible to obtain the α-type crystal by using a mixed solvent having a high ethanol content, to which ethanol is further added such that the volume ratio of water to ethanol is 1:12.5 or more. During this, when the dissolution, filtration and crystallization are carried out in a mixed solvent having a ratio of water to ethanol of about 1:10, the β-type crystal and γ-type crystal may possibly be formed.

Table 4 shows the melting point and solubility in water at room temperature of the three kinds of novel crystals of the potassium salt of Compound A according to the invention.

TABLE 4

| type of crystal | melting point/° C. | solubility in water at room temperature/ mg/mL |
|---|---|---|
| α-type crystal | 196–198 | 19.3 |
| β-type crystal | 231–233 | 9.0 |
| γ-type crystal | 251–254 | 6.9 |

As a result, it was revealed that the α-type crystal of the potassium salt of Compound A is the most excellent in water solubility and that the β-type crystal and γ-type crystal have a high melting point and are excellent in heat stability.

Figure 10:
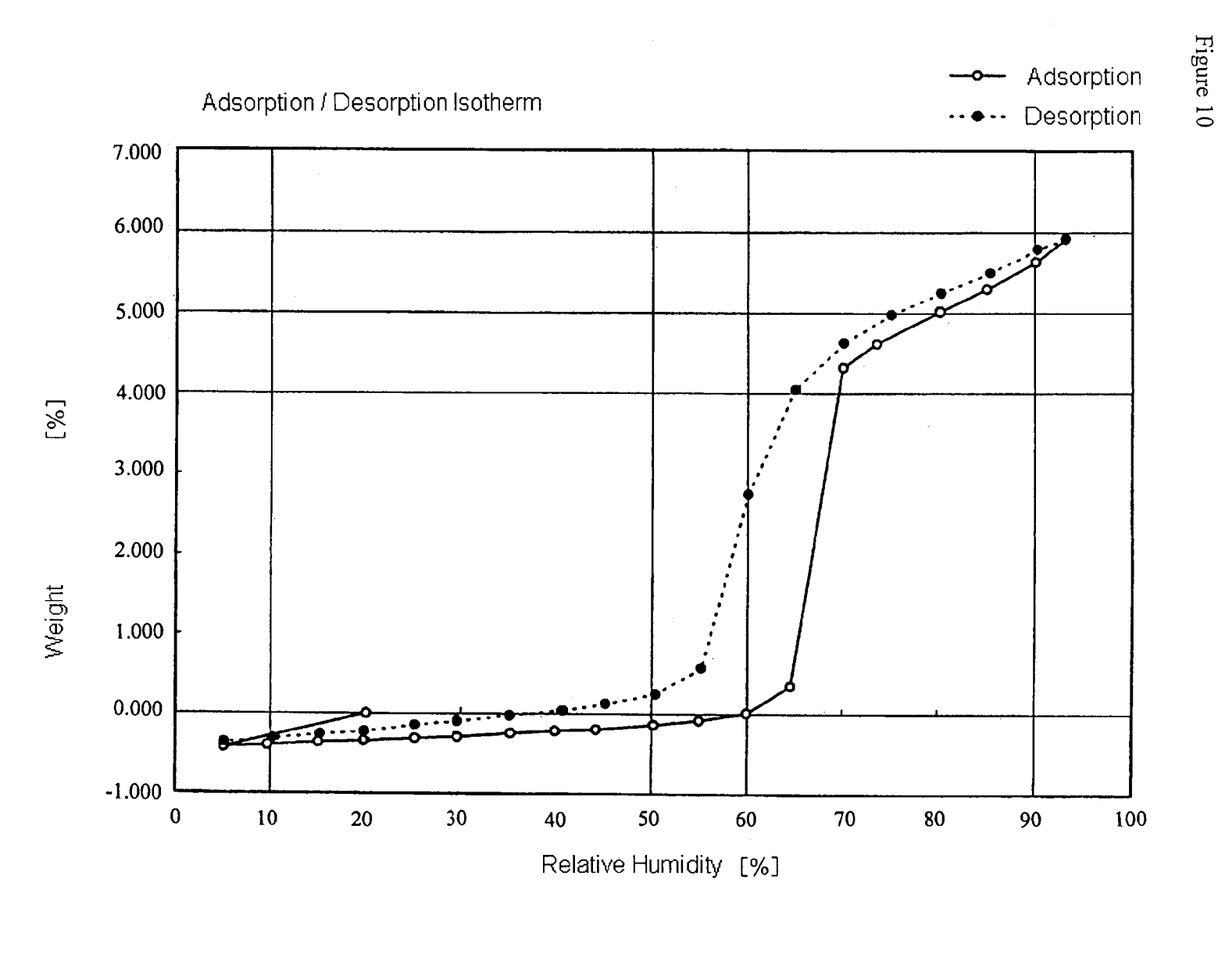
FIG. 10 is a chart to show the hygroscopicity of an α-type crystal of a potassium salt of Compound A (Example 4).
Figure 11:
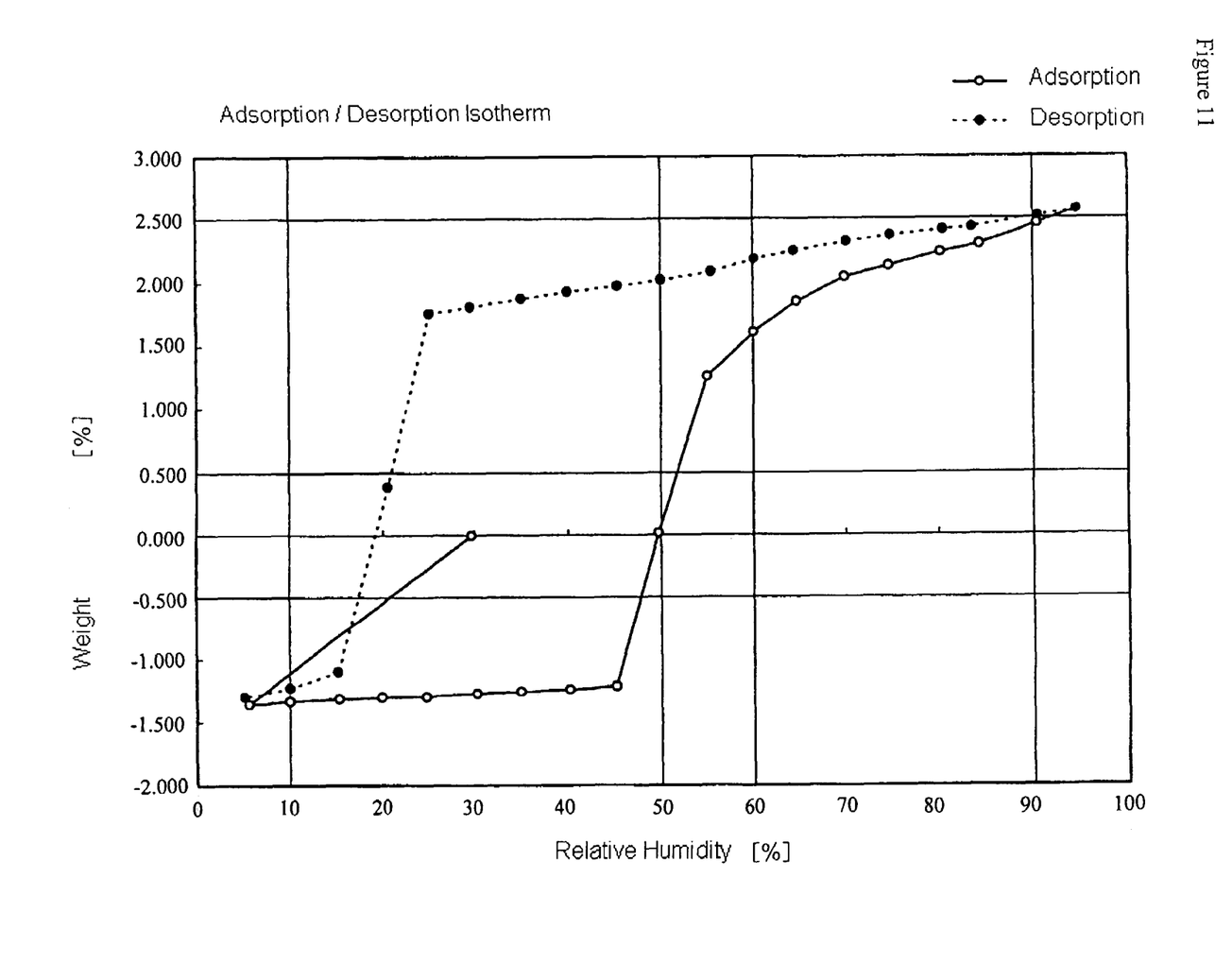
FIG. 11 is a chart to show the hygroscopicity of a β-type crystal of a potassium salt of Compound A (Example 6).
Figure 12:
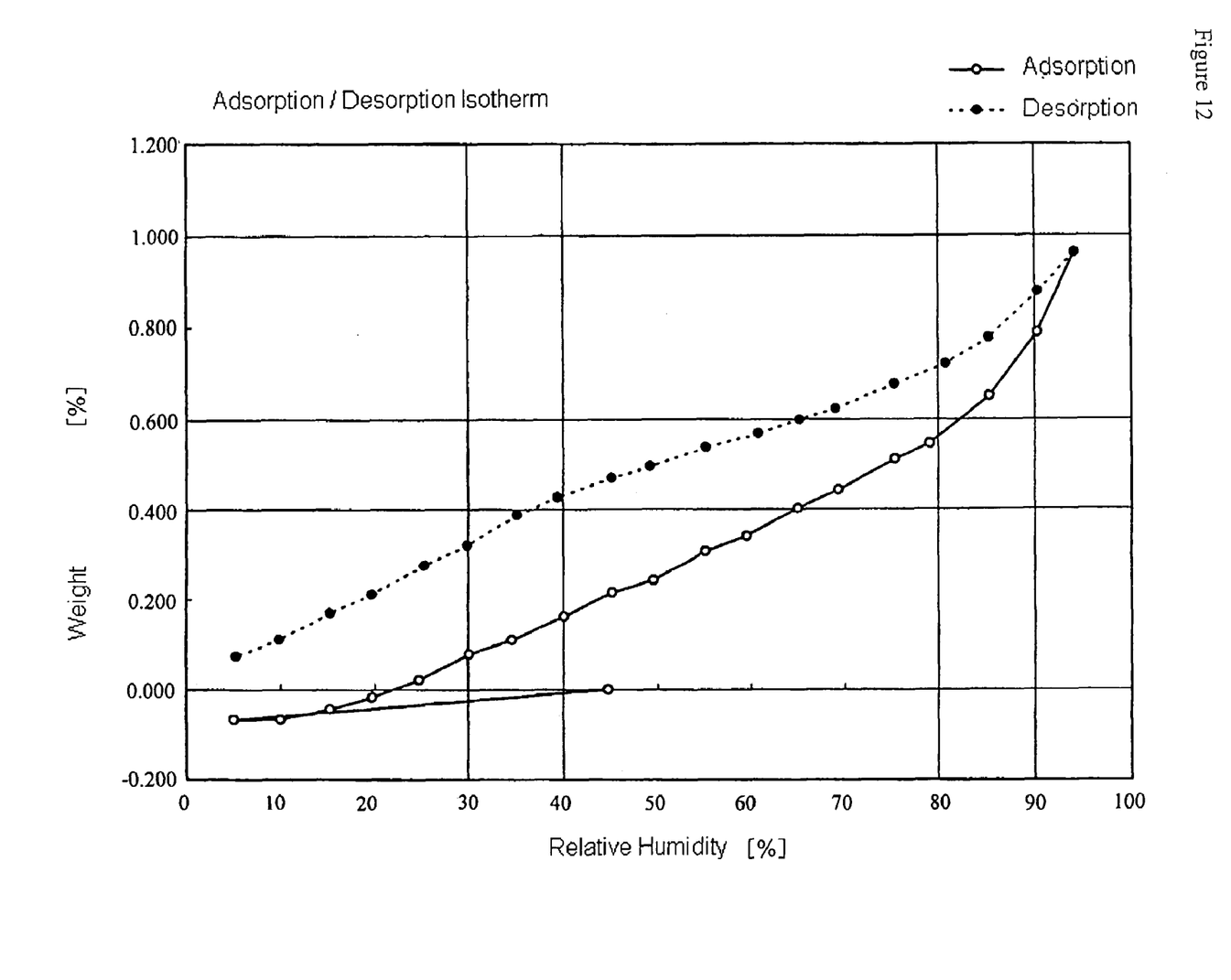
FIG. 12 is a chart to show the hygroscopicity of a γ-type crystal of a potassium salt of Compound A (Example 7).

Also, FIGS. 10 to 12 show the hygroscopicity of the three kinds of novel crystals of the potassium salt of Compound A of the invention. As a result, it was revealed that the γ-type crystal of the potassium salt of Compound A gradually absorbs moisture with an increase of the humidity but absorbs moisture only to an extent of about 1% (corresponding to 0.3 moles of water) and hence, is excellent in stability caused by the hygroscopicity. On the other hand, the α-type crystal of the potassium salt of Compound A abruptly absorbed moisture when the humidity exceeded 65%, and absorbed moisture to an extent of about 6% (corresponding to 1.8 moles of water). The β-type crystal of the potassium salt of Compound A gradually absorbed moisture when the humidity exceeded 45%, and absorbed moisture to an extent of about 4% (corresponding to 1.2 moles of water).

As to Compound A, a salt thereof, a solvate thereof or a solvate of a salt thereof, each of which is used during preparing the α-type crystal of the potassium salt of Compound A in the foregoing preparation process, it is industrially advantageous to use a Compound A 0.4 ethyl acetate or a Compound A monoethanolate, each of which does not require the purification operation by a column chromatography, as described previously.

The Compound A 0.4 ethyl acetate of the invention can be prepared by recrystallization from ethyl acetate or suspending in ethyl acetate upon heating during the purification of Compound A.

The Compound A monoethanolate can be prepared by recrystallization from ethanol or suspending in ethanol upon heating during the purification of Compound A, or by recrystallizing the Compound A 0.4 ethyl acetate from ethanol or suspending it in ethanol upon heating.

Table 5 shows the physicochemical properties of the two kinds of novel solvates of Compound A according to the invention.

TABLE 5

| | | purification effect by crystallization | |
|---|---|---|---|
| composition | melting point/° C. | purity/% | main impurity content/% |
| Compound A 0.4 ethyl acetate | 123–125 | 99.2 | 0.3 |
| Compound A monoethanolate | 99–101 | 98.7 | 0.7 |

In Table 5, the term "main impurity" means an impurity that is most contained during the purification and is a compound represented by the following structure.

"Main Impurity" in Table 5

As described above, the Compound A 0.4 ethyl acetate and the Compound A monoethanolate are advantageous in the preparation of the potassium salt of Compound A on the point that purification by a column chromatography which likely complicates the operation on the industrial manufacturing is not needed.

Also, especially in the pharmaceutical field, for the sake of providing a drug having high safety and bringing about an effective operation/working-effect, it is an important problem to keep the purity of its bulk higher.

On this point, since the Compound A 0.4 ethyl acetate is low in the impurity content as compared with the Compound A monoethanolate, during preparing the potassium salt of Compound A, it may be considered that when the Compound A 0.4 ethyl acetate is used, it is possible to reduce the impurity content by about 40% as compared with the case where the Compound A monoethanolate is used.

Also, it is possible to prevent excessive consumption of potassium hydroxide by ethyl acetate, which is used during preparing the potassium salt of Compound A using Compound A, a salt thereof, a solvate thereof or a solvate of a salt thereof as a process intermediate and to prevent contamination of ethyl acetate into the potassium salt of Compound A as a final body as the pharmaceutical bulk. Accordingly, it is also possible to convert the Compound A 0.4 ethyl acetate having a high degree of purification into the Compound A monoethanolate by solvent-mediated rearrangement and to provide it for the preparation of the potassium salt of Compound A. In this case, it is possible to prevent excessive consumption of potassium hydroxide to be used during preparing the potassium salt of Compound A and also to prevent contamination of ethyl acetate into the potassium salt of Compound A as the final bulk.

N-[6-Chloro-5-(2-methoxyphenoxy)-2-(2-pyrimidinyl)-4-pyrimidinyl]-2-phenylethenesulfonamide that can be the starting material of the compound of the invention can be prepared by the method described in Referential Example 1 of the foregoing document.

Since the α-type crystal of the potassium salt of Compound A of the invention has high water solubility as compared with β-type crystal and the γ-type crystal, it can be expected to have an operation/working-effect such as enhancement of absorption in oral drugs. Also, the β-type crystal of the potassium salt of Compound A of the invention is excellent in heat stability, and the γ-type crystal of Compound A is low in hygroscopicity and excellent in stability, and excellent in filtration performance in the industrial manufacturing because of low electrification and high fluidity. In addition, by preparing the α-type crystal, β-type crystal or γ-type crystal of the potassium salt of Compound A as a single crystal form in the foregoing preparation process, it is possible to ensure the constant quality required as drugs.

Additionally, the α-type crystal, β-type crystal and γ-type crystal of the potassium salt of Compound A of the invention are morphologically pure. Also, it is confirmed that the α-type crystal of the potassium salt of Compound A of the invention is stable over 2 years in the preservation state at normal temperature under atmospheric pressure in a reagent bottle. Moreover, since it is hardly electrified and is excellent in fluidity, it has advantages such that works are easy in adjusting solid formulations such as powders, granules, tablets, and capsules.

BEST MODE FOR CARRYING OUT THE INVENTION

The invention will be more specifically described below with reference to the following Examples.

Incidentally, the melting point measurement and DSC analysis were carried out in the following manners.

<Melting Point Measurement>

The respective crystal forms were measured for melting point according to the melting point measurement method (programming rate: 1° C./min) of the Pharmacopoeia of Japan, and the melting point of each of the crystal forms was specified based on the found value.

<TG-DSC Thermogravimetric Analysis>

Five milligrams of each of a sample and a standard substance (α-alumina for thermal analysis: $Al_2O_3$) was filled in a sample vessel, a heating furnace part was heated at a constant heating rate (10° C./min), and a change in quantity of heat (DSC) generated between the sample and the standard substance during the course of temperature change was continuously recorded. Incidentally, the treatment of the devices including data processing was followed according to the method and procedures instructed on each device (used instrument: TG8110).

EXAMPLE 1

In 100 mL of methanol was dissolved 8 g of potassium hydroxide, to which was then added 10 g of N-[6-chloro-5-(2-methoxyphenoxy)-2-(2-pyrimidinyl)-4-pyrimidinyl]-2-phenylethenesulfonamide with stirring at room temperature. The reaction mixture was stirred under reflux for 3 hours, and the solvent was then removed. To the residue were added ethyl acetate and aqueous hydrochloric acid upon heating, then an organic layer was separated, and the resulting organic layer (ethyl acetate solution) was allowed to stand for cooling to room temperature. A deposited crystal was collected by filtration and dried in vacuo to obtain 9.6 g of a Compound A 0.4 ethyl acetate. The melting point according to the foregoing melting point measurement method was from 123 to 125° C.

The elemental analysis values of this compound are shown in Table 7.

TABLE 7

| As Compound A 0.4 ethyl acetate ($C_{24}H_{21}N_5O_5S \cdot 0.4\ C_4H_8O_2$) | | | | | |
|---|---|---|---|---|---|
| | C(%) | H(%) | N(%) | O(%) | S(%) |
| calculated values | 58.37 | 4.63 | 13.30 | 17.62 | 6.09 |
| obtained values | 58.16 | 4.56 | 13.12 | | 5.96 |

EXAMPLE 2

In 100 mL of methanol was dissolved 8 g of potassium hydroxide, to which was then added 10 g of N-[6-chloro-5-(2-methoxyphenoxy)-2-(pyrimidin-2-yl)pyrimidin-4-yl]-2-phenylethenesulfonamide with stirring at room temperature. The reaction mixture was stirred under reflux for 3 hours, and the solvent was then removed. To the residue were added ethyl acetate and hydrochloric acid water upon heating, then an organic layer was separated. The resulting organic layer (ethyl acetate solution) was concentrated, and ethanol was added to the residue, followed by stirring upon heating. After allowing to stand for cooling to room temperature, a deposited crystal was collected by filtration and dried in vacuo to obtain 10.3 g of a Compound A monoethanolate. The melting point according to the foregoing melting point measurement method was from 99 to 101° C.

The elemental analysis values of this compound are shown in Table 6.

TABLE 6

As Compound A monoethanolate ($C_{24}H_{21}N_5O_5S.1.0\ C_2H_5OH$)

|  | C(%) | H(%) | N(%) | O(%) | S(%) |
|---|---|---|---|---|---|
| calculated values | 58.09 | 5.06 | 13.03 | 17.86 | 5.96 |
| obtained values | 57.87 | 4.91 | 13.12 |  | 6.08 |

EXAMPLE 3

10 g of the compound of Example 1 was added to 100 mL of ethanol, and the mixture was stirred under reflux for one hour, followed by allowing to stand for cooling to room temperature. A deposited crystal was collected by filtration and dried in vacuo to obtain 9.6 g of a Compound A monoethanolate.

The elemental analysis values of this compound were the same as in the compound of Example 2.

EXAMPLE 4

Potassium hydroxide (1.3 g) was dissolved in 150 mL of ethanol and 15 mL of water, to which was then added 10 g the compound of Example 1 with stirring at room temperature, and the mixture was completely dissolved with stirring upon heating. After thermal filtration, 50 mL of hot ethanol was added to the filtrate, and the mixture was allowed to stand for cooling. A deposited crystal was collected by filtration and dried in vacuo to obtain 9.5 g of an α-type crystal of a potassium salt of Compound A. The melting point according to the foregoing melting point measurement method was from 196 to 198° C.

Figure 1:
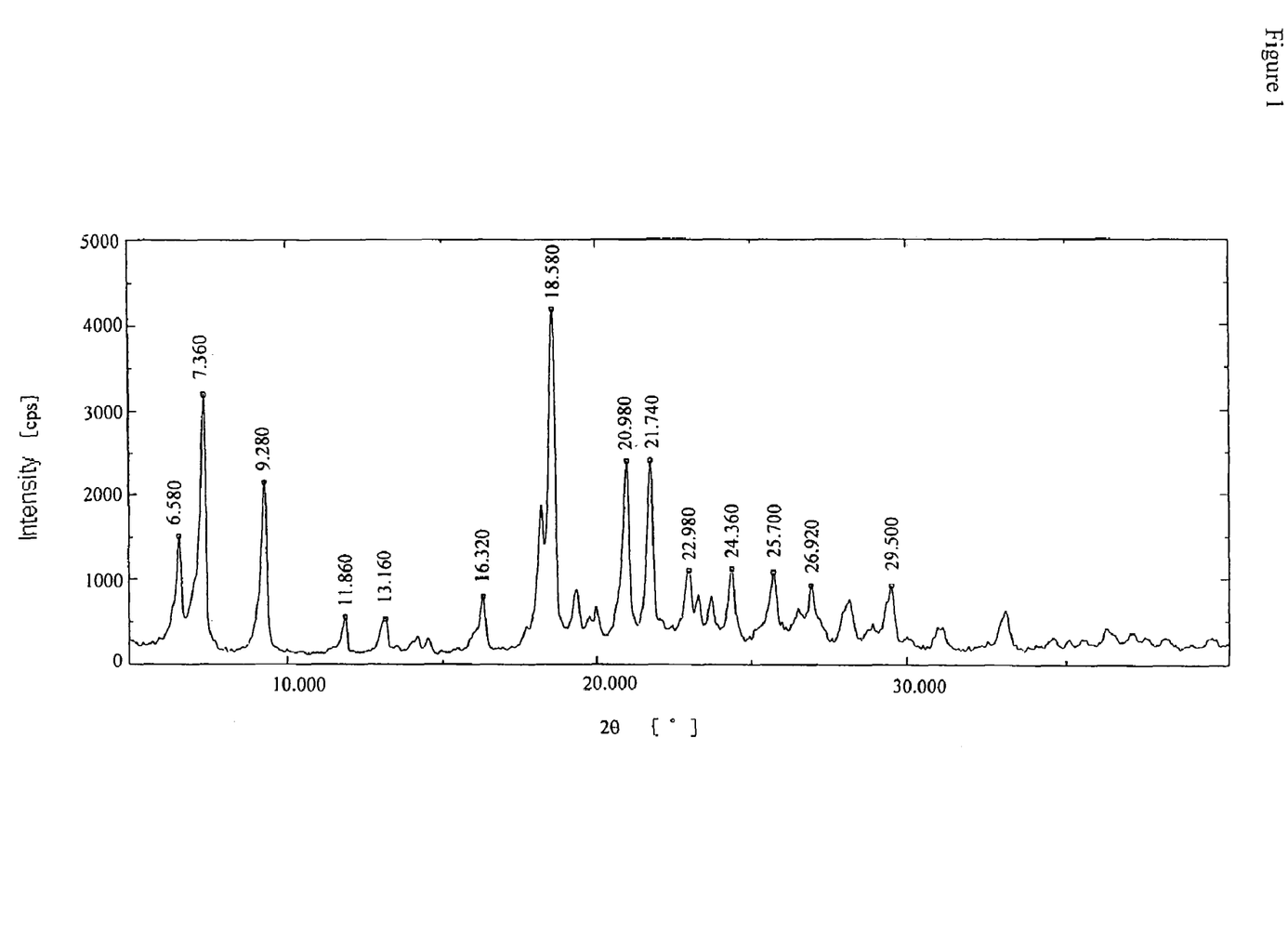
FIG. 1 is a chart to show the powder X-ray diffraction analysis date of an α-type crystal of a potassium salt of Compound A (Example 4), in which the ordinate stands for an X-ray intensity, and the abscissa stands for a diffraction angle (2θ).
Figure 4:
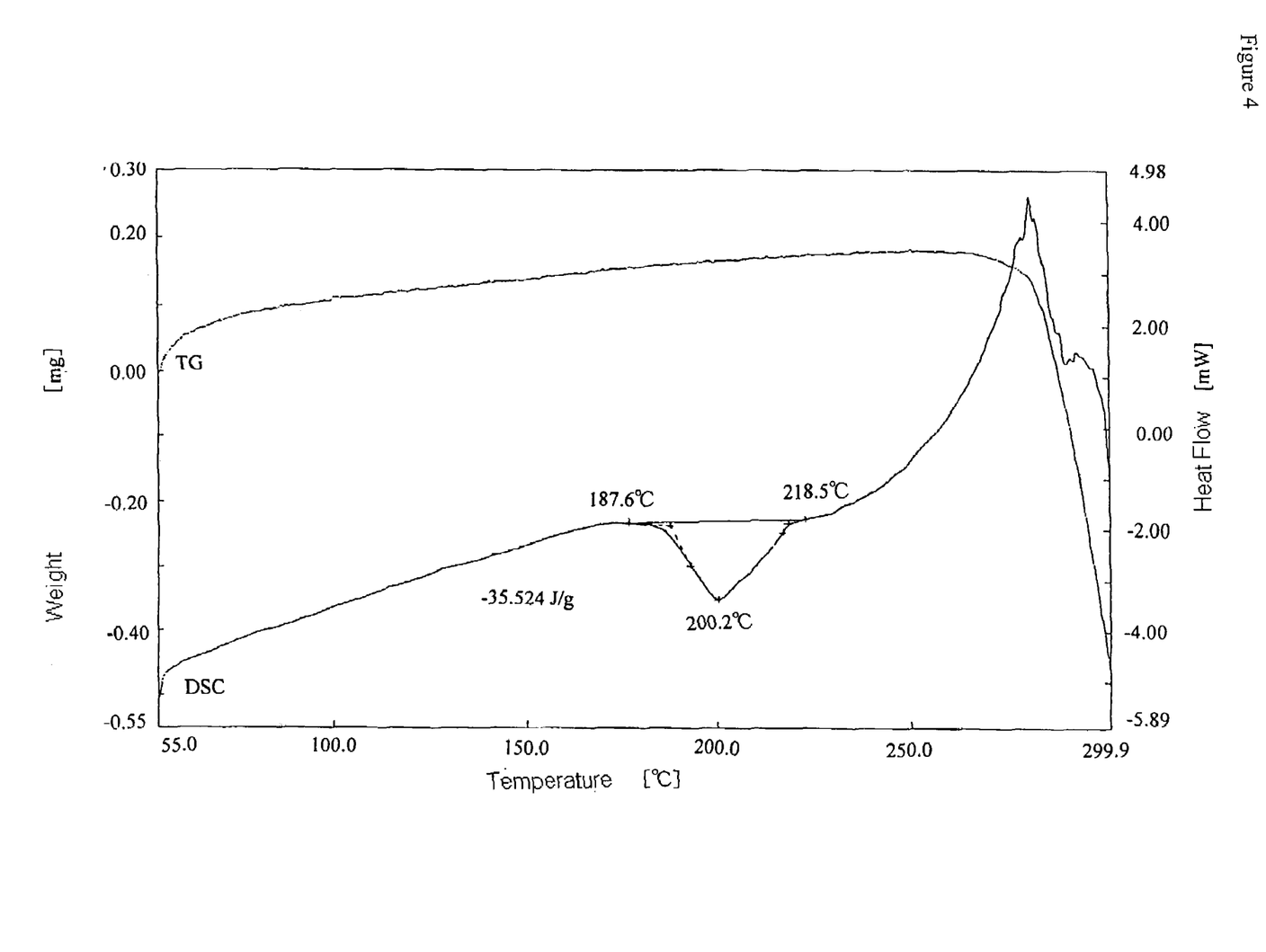
FIG. 4 is a chart to show the TG-DSC thermogravimetric analysis of an α-type crystal of a potassium salt of Compound A (Example 4).
Figure 7:
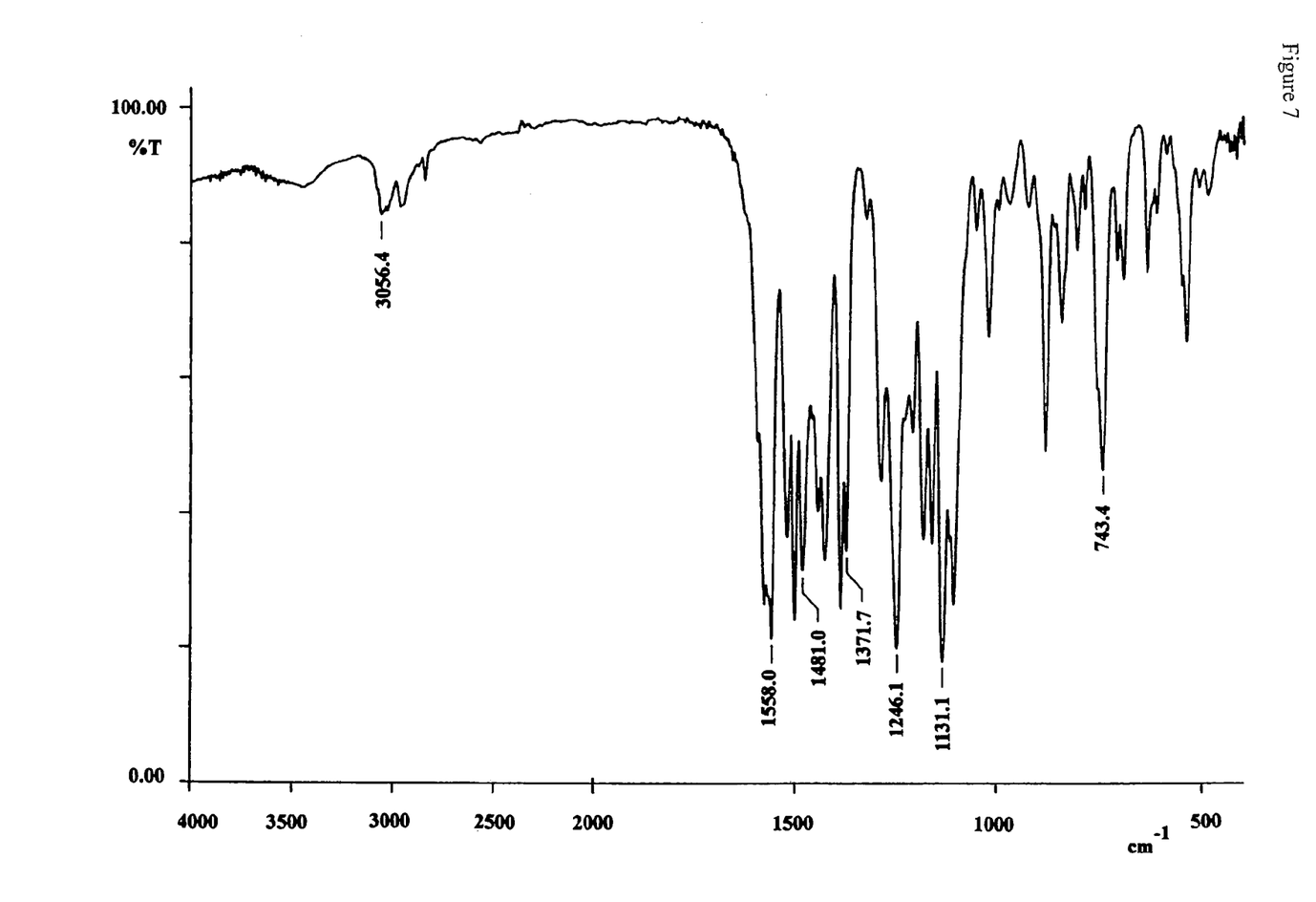
FIG. 7 is a chart to show the infrared absorption spectrum of an α-type crystal of a potassium salt of Compound A (Example 4).

With respect to this compound, the elemental analysis values are shown in Table 8, the powder X-ray diffraction data are shown in FIG. 1, the results of TG-DSC thermogravimetric analysis are shown in FIG. 4, the infrared absorption spectrum is shown in FIG. 7, and the hygroscopicity data are shown in FIG. 10, respectively.

TABLE 8

As potassium salt of Compound A ($C_{24}H_{20}KN_5O_5S$)

|  | C(%) | H(%) | N(%) | O(%) | S(%) | K(%) |
|---|---|---|---|---|---|---|
| calculated values | 54.43 | 3.81 | 13.22 | 15.10 | 6.05 | 7.38 |
| obtained values | 54.29 | 3.79 | 13.22 |  | 6.05 |  |

EXAMPLE 5

Potassium hydroxide (1.3 g) was dissolved in 150 mL of ethanol and 15 mL of water, to which was then added 10 g the compound of Example 3 with stirring at room temperature, and the mixture was completely dissolved with stirring upon heating. After thermal filtration, 50 mL of hot ethanol was added to the filtrate, and the mixture was allowed to stand for cooling. A deposited crystal was collected by filtration and dried in vacuo to obtain 9.4 g of an α-type crystal of a potassium salt of Compound A.

With respect to this compound, the elemental analysis values, the powder X-ray diffraction data, the TG-DSC thermogravimetric analysis data, the infrared absorption spectrum, and the hygroscopicity data are the same as in the compound of Example 4.

EXAMPLE 6

Potassium hydroxide (1.3 g) was dissolved in 50 mL of ethanol and 50 mL of water, to which was then added 10 g the compound of Example 1 with stirring at room temperature, and the mixture was completely dissolved with stirring upon heating. After thermal filtration, the filtrate was rapidly cooled in an ice water bath at about 0° C., to start crystallization at lower than 10° C. A deposited crystal was collected by filtration and dried in vacuo to obtain 6.7 g of a β-type crystal of a potassium salt of Compound A. The melting point according to the foregoing melting point measurement method was from 231 to 233° C.

Figure 2:
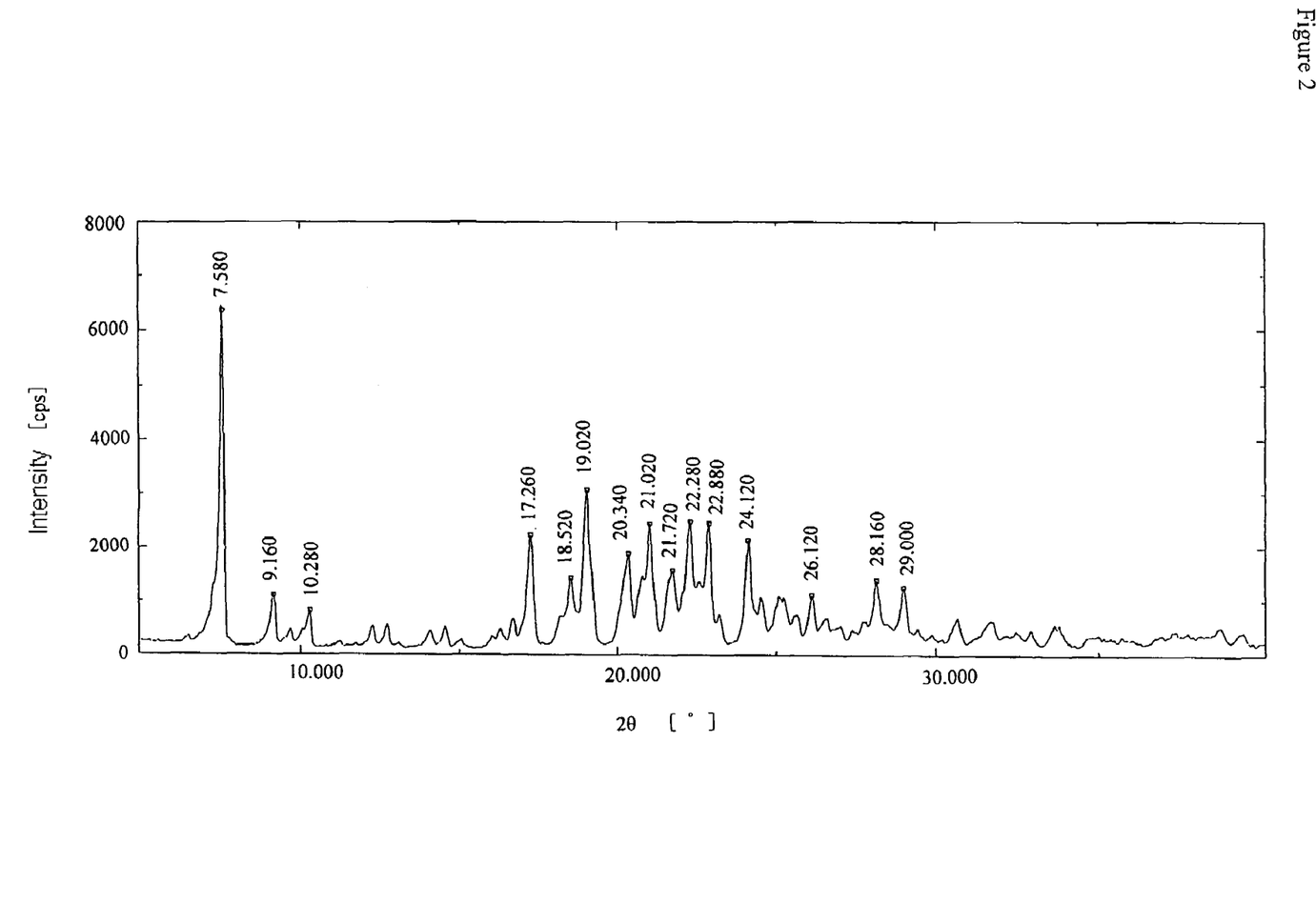
FIG. 2 is a chart to show the powder X-ray diffraction analysis date of a β-type crystal of a potassium salt of Compound A (Example 6), in which the ordinate stands for an X-ray intensity, and the abscissa stands for a diffraction angle (2θ).
Figure 5:
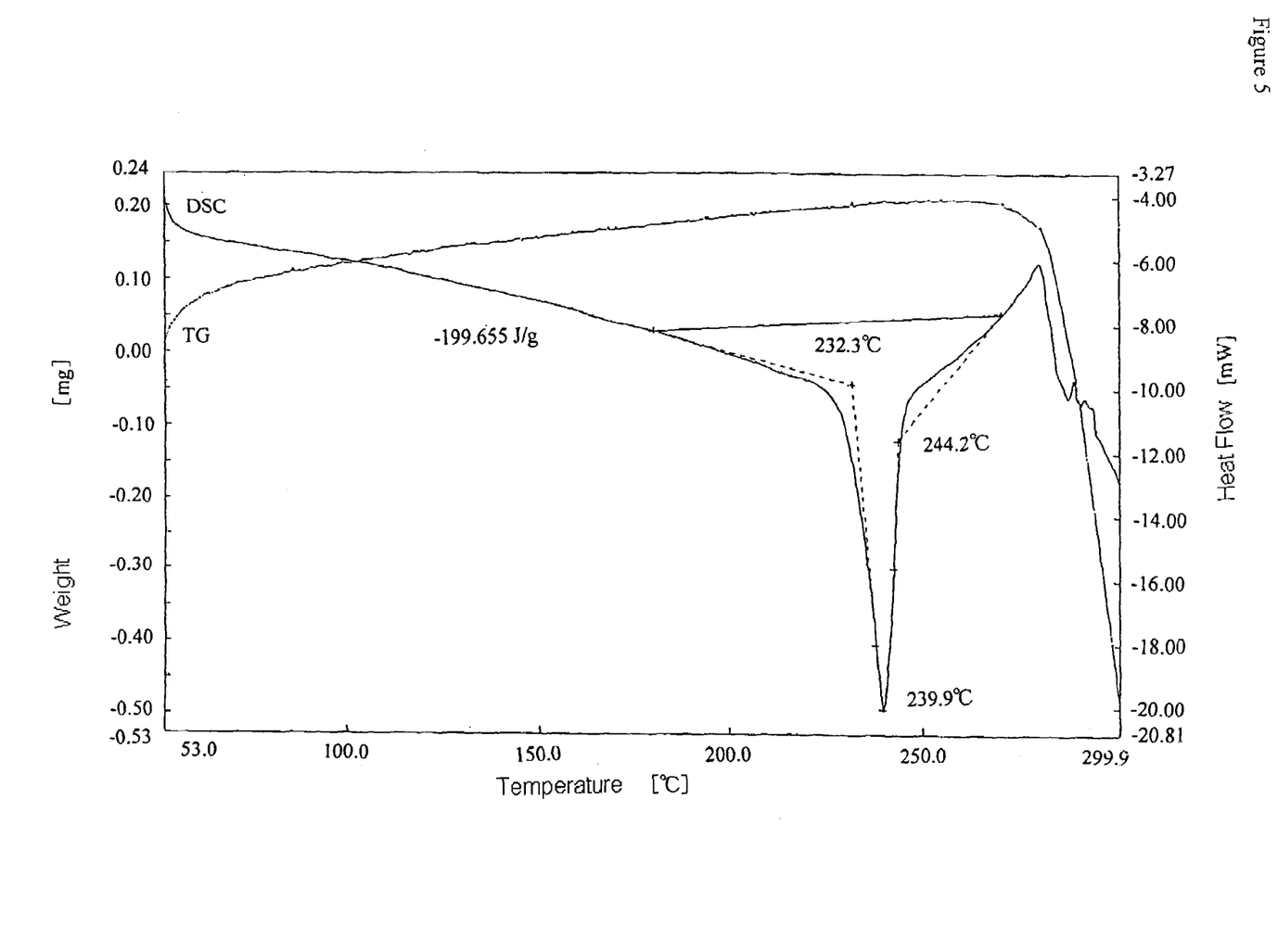
FIG. 5 is a chart to show the TG-DSC thermogravimetric analysis of a β-type crystal of a potassium salt of Compound A (Example 6).
Figure 8:
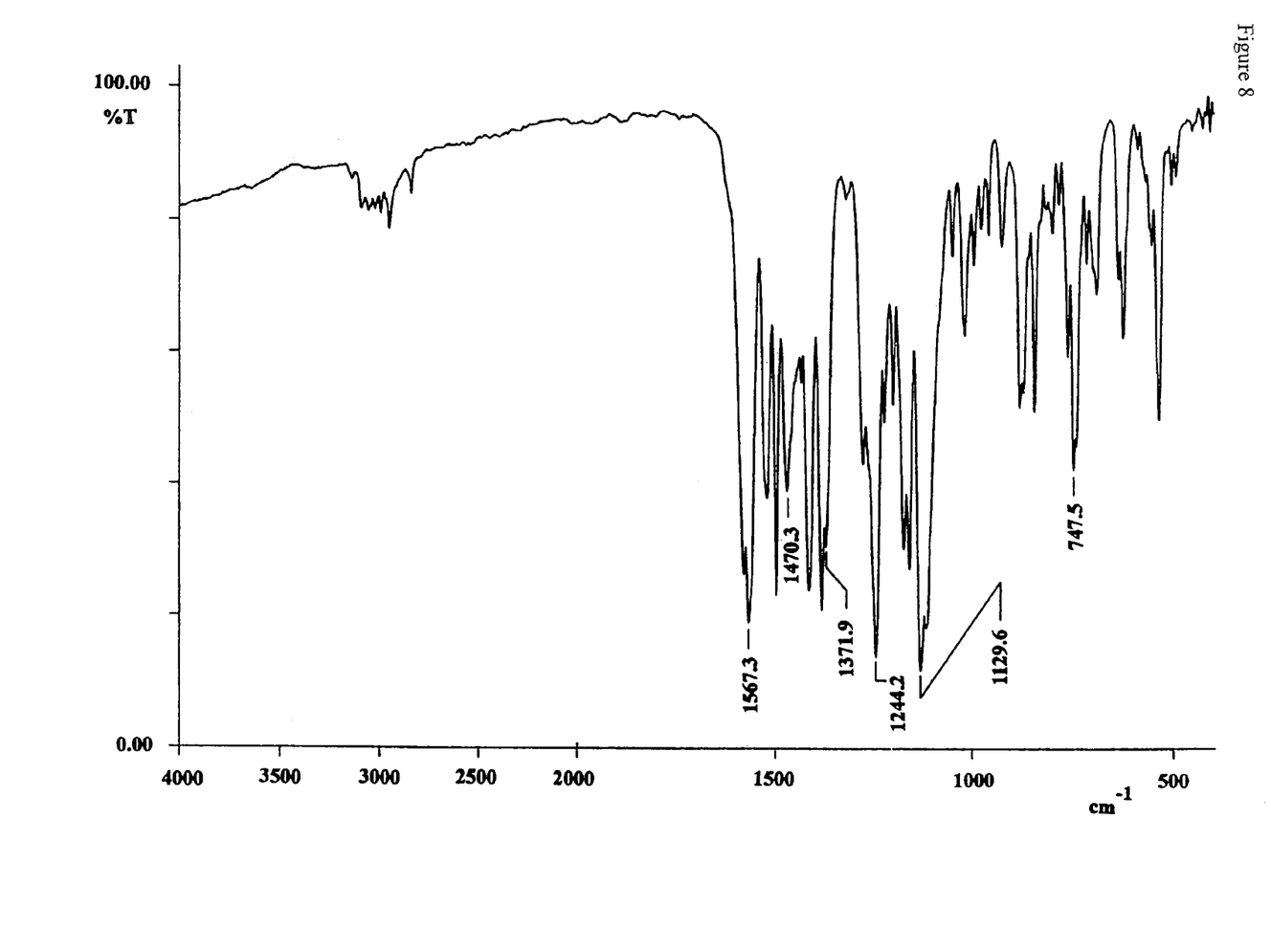
FIG. 8 is a chart to show the infrared absorption spectrum of a β-type crystal of a potassium salt of Compound A (Example 6).

With respect to this compound, the powder X-ray diffraction data are shown in FIG. 2, the results of TG-DSC thermogravimetric analysis are shown in FIG. 5, the infrared absorption spectrum is shown in FIG. 8, and the hygroscopicity data are shown in FIG. 11, respectively.

EXAMPLE 7

Potassium hydroxide (1.3 g) was dissolved in 100 mL of methanol and 100 mL of water, to which was then added 10 g the compound of Example 1 with stirring at room temperature., and the mixture was completely dissolved with stirring upon heating. After thermal filtration, a crystal deposited in a water bath at about 20° C. was collected by filtration and dried in vacuo to obtain 7.9 g of a γ-type crystal of a potassium salt of Compound A. The melting point according to the foregoing melting point measurement method was from 251 to 254° C.

Figure 3:
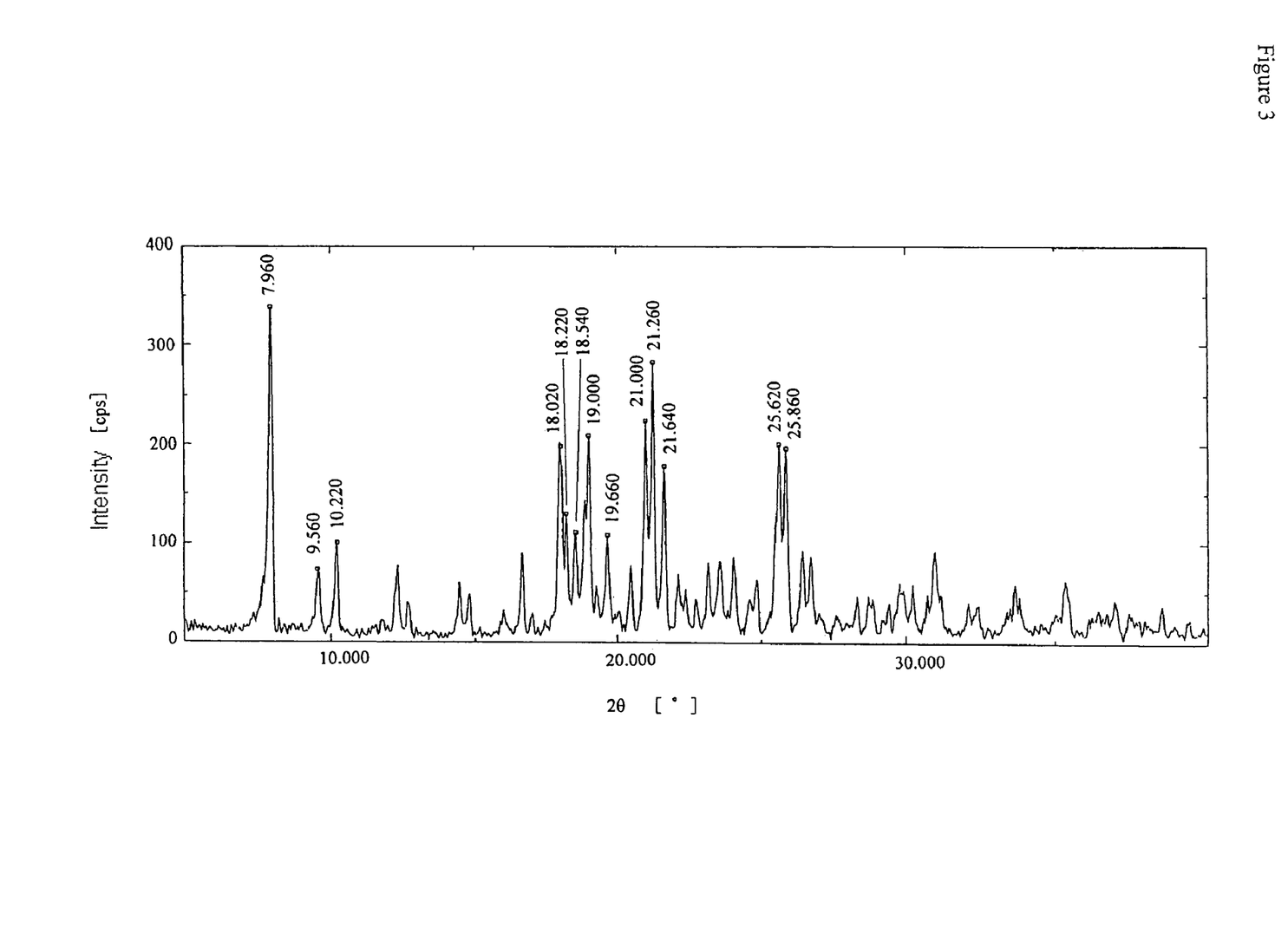
FIG. 3 is a chart to show the powder X-ray diffraction analysis date of a γ-type crystal of a potassium salt of Compound A (Example 7), in which the ordinate stands for an X-ray intensity, and the abscissa stands for a diffraction angle (2θ).
Figure 6:
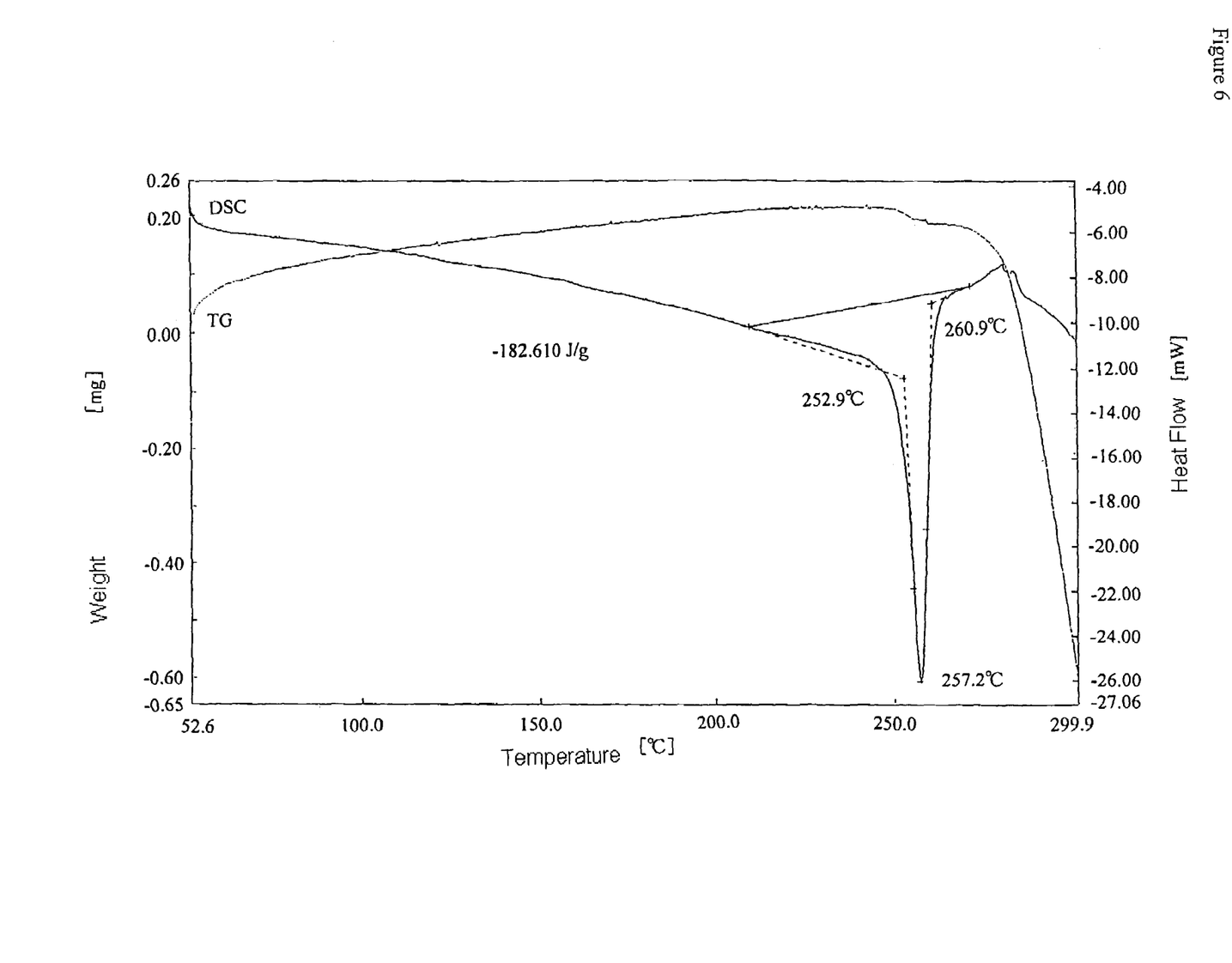
FIG. 6 is a chart to show the TG-DSC thermogravimetric analysis of a γ-type crystal of a potassium salt of Compound A (Example 7).
Figure 9:
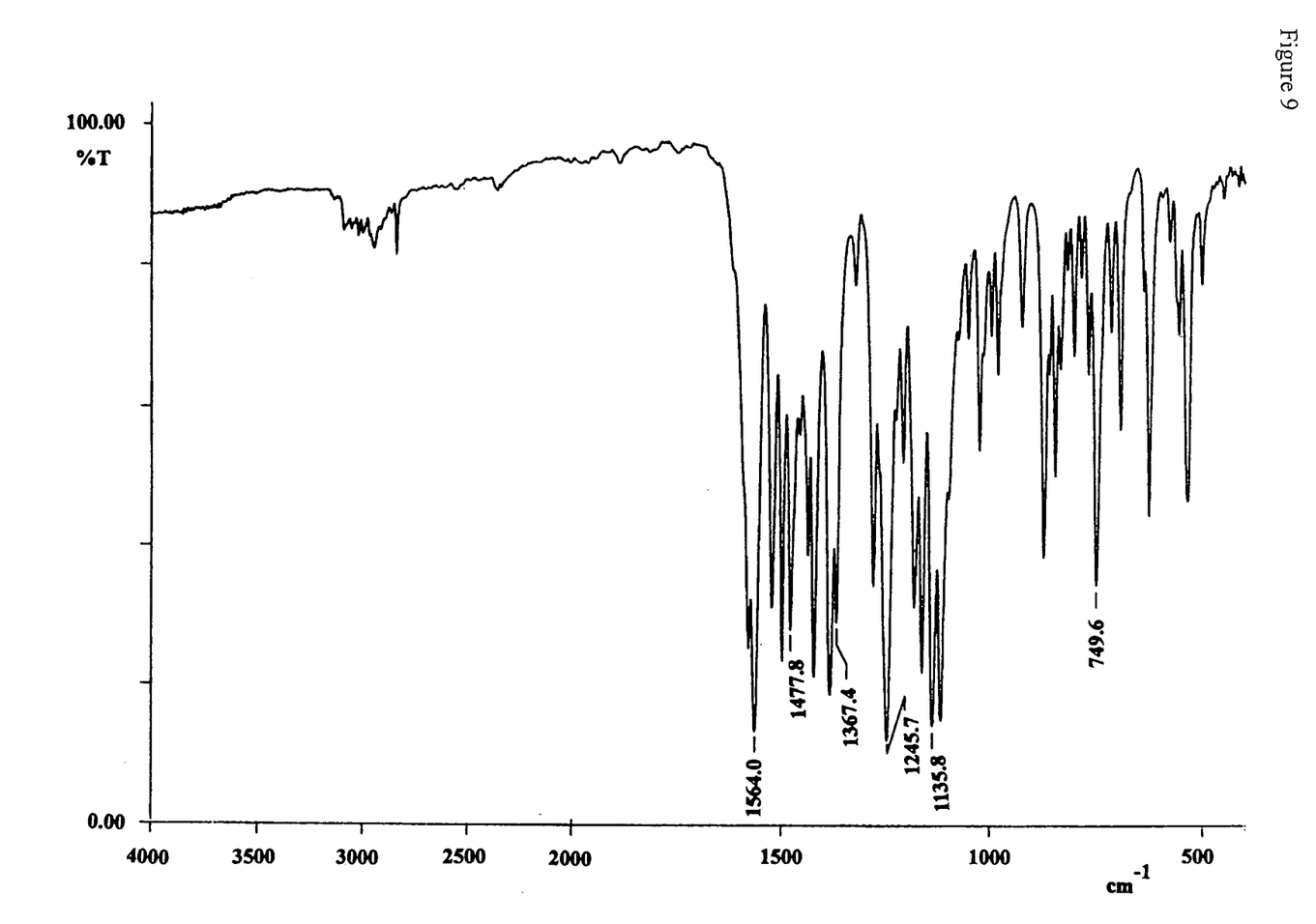
FIG. 9 is a chart to show the infrared absorption spectrum of a γ-type crystal of a potassium salt of Compound A (Example 7).

With respect to this compound, the powder X-ray diffraction data are shown in FIG. 3, the results of TG-DSC thermogravimetric analysis are shown in FIG. 6, the infrared absorption spectrum is shown in FIG. 9, and the hygroscopicity data are shown in FIG. 12, respectively.

INDUSTRIAL APPLICABILITY

According to the invention, there are provided an α-type crystal of a potassium salt of Compound A useful as an active ingredient of drugs, which is industrially advantageous on the manufacturing, is advantageous from the viewpoint of formulation because of its high solubility, and is expected to have good oral absorption; a β-type crystal of a potassium salt of Compound A useful as an active ingredient of drugs, which has a high melting point and is excellent in heat stability; and a γ-type crystal of a potassium salt of Compound A useful as an active ingredient of Compound A, which is excellent in stability because of its high melting point and low hygroscopicity and is excellent in industrial manufacturing, especially filtration performance because of its low electrification and high fluidity. In addition, according to the preparation process for an α-type crystal, a β-type crystal or a γ-type crystal of a potassium salt of Compound A of the invention, it is possible to prepare an α-type crystal, a β-type crystal or a γ-type crystal of a potassium salt of Compound A in a single crystal form on an industrially large scale.

Also, according to the invention, it is possible to prepare Compound A, a salt thereof, a solvate thereof or a solvate of a salt thereof as process intermediates of a potassium salt of Compound A useful as an active ingredient of drugs, without need of undesired purification by a column chromatography which complicates the operation in the industrial manufacturing course. There are provided a Compound A 0.4 ethyl acetate and a Compound A monoethanolate. Above all, the Compound A 0.4 ethyl acetate is high in degree of purification as compared with the Compound A monoethanolate; and the Compound A monoethanolate can prevent excessive consumption of potassium hydroxide to be used during the preparation of the potassium salt of Compound A and prevent contamination of ethyl acetate into the final bulk.

The invention claimed is:

1. An α-type crystal of a potassium salt of (E)-N-[6-methoxy-5-(2-methoxyphenoxy)-2-(pyrimidin-2-yl)pyrimidin-4-yl]-2-phenylethene-sulfonamide in substantially pure form.

2. An α-type crystal of a potassium salt of (E)-N-[6-methoxy-5-(2-methoxyphenoxy)-2-(pyrimidin-2-yl)pyrimidin-4-yl]-2-phenylethene-sulfonamide, characterized by having a melting point of from 196 to 198° C. and main peaks in the vicinity of lattice spacings of 12.00, 9.52, 4.77, 4.34 and 4.08 angstroms in the powder X-ray diffraction spectrum obtained using a Cu—Kα line.

3. The α-type crystal according to claim 2, characterized by having the lattice spacings and relative intensities shown in Table 9 in the powder X-ray diffraction spectrum obtained using a Cu—Kα line.

TABLE 9

| lattice spacing/Å | relative intensity | lattice spacing/Å | relative intensity |
|---|---|---|---|
| 13.42 | slightly strong | 4.23 | strong |
| 12.00 | strong | 4.08 | strong |
| 9.52 | strong | 3.87 | slightly strong |
| 7.46 | medium | 3.65 | slightly strong |
| 6.72 | medium | 3.46 | slightly strong |
| 5.43 | medium | 3.31 | medium |
| 4.77 | strong | 3.03 | medium |

4. A β-type crystal of a potassium salt of (E)-N-[6-methoxy-5-(2-methoxyphenoxy)-2-(pyrimidin-2-yl)pyrimidin-4-yl]-2-phenylethene-sulfonamide in substantially pure form.

5. A β-type crystal of a potassium salt of (E)-N-[6-methoxy-5-(2-methoxyphenoxy)-2-(pyrimidin-2-yl)pyrimidin-4-yl]-2-phenylethene-sulfonamide, characterized by having a melting point of 231 to 233° C. and main peaks in the vicinity of lattice spacings of 11.65 and 4.66 angstroms in the powder X-ray diffraction spectrum obtained using a Cu—Kα line.

6. The β-type crystal according to claim 5, characterized by having the lattice spacings and relative intensities shown in Table 10 in the powder X-ray diffraction spectrum obtained using a Cu—Kα line.

TABLE 10

| lattice spacing/Å | relative intensity | lattice spacing/Å | relative intensity |
|---|---|---|---|
| 11.65 | strong | 4.09 | medium |
| 9.65 | medium | 3.99 | slightly strong |
| 8.60 | medium | 3.88 | slightly strong |
| 5.13 | slightly strong | 3.69 | slightly strong |
| 4.79 | medium | 3.41 | medium |
| 4.66 | strong | 3.17 | medium |
| 4.36 | medium | 3.08 | medium |
| 4.22 | slightly strong | | |

7. A γ-type crystal of a potassium salt of (E)-N-[6-methoxy-5-(2-methoxyphenoxy)-2-(pyrimidin-2-yl)pyrimidin-4-yl]-2-phenylethene-sulfonamide in substantially pure form.

8. A γ-type crystal of a potassium salt of (E)-N-[6-methoxy-5-(2-methoxyphenoxy)-2-(pyrimidin-2-yl)pyrimidin-4-yl]-2-phenylethene-sulfonamide, characterized by having a melting point of 251 to 254° C. and main peaks in the vicinity of lattice spacings of 11.10, 4.92, 4.67, 4.23, 4.18, 4.10, 3.47 and 3.44 angstroms in the powder X-ray diffraction spectrum obtained using a Cu—Kα line.

9. A γ-type crystal according to claim 8, characterized having the lattice spacings and relative intensities shown in Table 11 in the powder X-ray diffraction spectrum obtained using a Cu—Kα line.

TABLE 11

| lattice spacing/Å | relative intensity | lattice spacing/Å | relative intensity |
|---|---|---|---|
| 11.10 | strong | 4.51 | slightly strong |
| 9.24 | medium | 4.23 | strong |
| 8.65 | slightly strong | 4.18 | strong |
| 4.92 | strong | 4.10 | strong |
| 4.87 | slightly strong | 3.47 | strong |
| 4.78 | slightly strong | 3.44 | strong |
| 4.67 | strong | | |

10. A preparation process of the α-type crystal of a potassium salt of (E)-N-[6-methoxy-5-(2-methoxyphenoxy)-2-(pyrimidin-2-yl)pyrimidin-4-yl]-2-phenylethenesulfonamide according to claim 2 or claim 3, characterized by exerting potassium hydroxide or potassium carbonate to (E)-N-[6-methoxy-5-(2-methoxyphenoxy)-2-(pyrimidin-2-yl)pyrimidin-4-yl]-2-phenylethenesulfonamide, a salt thereof, a solvate thereof or a solvate of a salt thereof in an ethanol-water mixed solvent, dissolving therein, and then crystallizing out of the solution in a water-ethanol mixed solvent having a ratio of water to ethanol of 1:12.5 or more.

11. A preparation process of the α-type crystal of a potassium salt of (E)-N-[6-methoxy-5-(2-methoxyphenoxy)-2-(pyrimidin-2-yl)pyrimidin-4-yl]-2-phenylethenesulfonamide according to claims 2 or claim 3, characterized by exerting potassium hydroxide to (E)-N-[6-methoxy-5-(2-methoxyphenoxy)-2-(pyrimidin -2-yl)pyrimidin-4-yl]-2-phenylethenesulfonamide 0.4 ethyl acetate or a (E)-N-[6-methoxy -5-(2-methoxyphenoxy)-2-(pyrimidin-2-yl) pyrimidin-4-yl]-2-phenylethenesulfonamide monoethanolate in an ethanol-water mixed solvent, dissolving therein, and then crystallizing out of the solution in a water-ethanol mixed solvent having a ratio of water to ethanol of 1:12.5 or more.

12. (E)-N-[6-methoxy-5-(2-methoxyphenoxy)-2-(pyrimidin-2-yl)pyrimidin-4-yl]-2-phenylethenesulfonamide ethyl acetate.

13. (E)-N-[6-methoxy-5-(2-methoxyphenoxy)-2-(pyrimidin-2-yl )pyrimidin-4-yl]-2-phenylethenesulfonamide 0.4 ethyl acetate.

14. (E)-N-[6-methoxy-5-(2-methoxyphenoxy)-2-(pyrimidin-2-yl)pyrimidin-4-yl]-2-phenylethenesulfonamide ethanolate.

15. (E)-[6-methoxy-5-(2-methoxphenoxy)-2-(pyrimidin-2-yl)pyrimidin-4-yl]-2-phenylethenesulfonamide monoethanolate.

* * * * *